United States Patent
Nakamura et al.

(10) Patent No.: US 9,522,991 B2
(45) Date of Patent: Dec. 20, 2016

(54) CELLULOSE SOLUTION MANUFACTURING METHOD, CELLULOSE PRECIPITATE MANUFACTURING METHOD, CELLULOSE SACCHARIFICATION METHOD, CELLULOSE SOLUTION, AND CELLULOSE PRECIPITATE

(75) Inventors: Kenji Nakamura, Imabari (JP); Seiji Higaki, Imabari (JP); Manami Yatsuzuka, Imabari (JP); Kazuo Doyama, Tsukuba (JP); Kazuyoshi Iwane, Kyoto (JP); Masaki Takao, Tokyo (JP)

(73) Assignees: EHIME PREFECTURAL GOVERNMENT, Ehime (JP); SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 13/703,125

(22) PCT Filed: Sep. 22, 2011

(86) PCT No.: PCT/JP2011/071648
§ 371 (c)(1),
(2), (4) Date: Apr. 2, 2013

(87) PCT Pub. No.: WO2012/039462
PCT Pub. Date: Mar. 29, 2012

(65) Prior Publication Data
US 2013/0177948 A1 Jul. 11, 2013

(30) Foreign Application Priority Data
Sep. 24, 2010 (JP) ................. 2010-214124

(51) Int. Cl.
| | | |
|---|---|---|
| C08L 1/02 | (2006.01) | |
| C12P 19/02 | (2006.01) | |
| C12P 19/14 | (2006.01) | |
| C13K 1/02 | (2006.01) | |
| C08B 1/00 | (2006.01) | |
| C08H 1/00 | (2006.01) | |
| D21C 1/08 | (2006.01) | |
| D21C 3/02 | (2006.01) | |
| D21C 5/02 | (2006.01) | |
| C08H 8/00 | (2010.01) | |

(52) U.S. Cl.
CPC ............... *C08L 1/02* (2013.01); *C08B 1/003* (2013.01); *C08H 8/00* (2013.01); *C12P 19/02* (2013.01); *C12P 19/14* (2013.01); *C13K 1/02* (2013.01); *D21C 1/08* (2013.01); *D21C 3/02* (2013.01); *D21C 3/028* (2013.01); *D21C 5/02* (2013.01); *C12P 2201/00* (2013.01); *C12P 2203/00* (2013.01); *Y02W 30/648* (2015.05)

(58) Field of Classification Search
None
See application file for complete search history.

(56) References Cited

U.S. PATENT DOCUMENTS

| | | | |
|---|---|---|---|
| 2009/0286295 A1* | 11/2009 | Medoff et al. ............ | 435/162 |
| 2010/0159521 A1* | 6/2010 | Cirakovic et al. ........ | 435/72 |
| 2010/0159522 A1 | 6/2010 | Cirakovic | |
| 2012/0118518 A1 | 5/2012 | Calais et al. | |

FOREIGN PATENT DOCUMENTS

| | | |
|---|---|---|
| CN | 101649569 | 2/2010 |
| CN | 101649570 | 2/2010 |
| FR | 2 937 656 | 4/2010 |
| JP | 59-047201 | 3/1984 |
| JP | 04-293901 | 10/1992 |
| JP | 09-316101 | 12/1997 |
| JP | 2001-95594 | 4/2001 |
| JP | 2008-280635 | 11/2008 |
| JP | 2009-203454 | 9/2009 |

OTHER PUBLICATIONS

Andersson E et al. Energy efficient upgrading of biofuel integrated with a pulp mill. 2006. Energy. 31:1384-1394.*
Zhang S et al., "Dissolution behaviour and solubility of cellulose in NaOH complex solution", 2010. Carbohydrate Polymers. 81:668-674.*
International Search Report issued Nov. 1, 2011 in International (PCT) Application No. PCT/JP2011/071648.
Extended European Search Report issued Nov. 26, 2014 in corresponding European Application No. 11826907.5.
Tetsuo Kondo et al., "Characterization of Water-Soluble Cellulose Derivatives Produced by Alkali Treatment of Ozonized Allylated Celluloses", Journal of Applied Polymer Science, Wiley, US, vol. 36, No. 5, Aug. 20, 1988, pp. 1107-1112.
Daniella L. Morgado et al., "Bio-based Films from Linter Cellulose and Its Acetates: Formation and Properties", Materials, 2013, 6, pp. 2410-2435.

(Continued)

*Primary Examiner* — Paul Holland
(74) *Attorney, Agent, or Firm* — Wenderoth, Lind & Ponack, L.L.P.

(57) ABSTRACT

The invention relates to a cellulose solution manufacturing method including: performing an ozonation treatment to bring a cellulose-containing material and ozone into contact with each other; and performing an alkali treatment to bring the obtained treated material and an alkali aqueous solution into contact with each other, thereby dissolving at least cellulose in the cellulose-containing material brought into contact with the ozone in the alkali aqueous solution. According to the invention, it is possible to provide a method of manufacturing a cellulose solution in which cellulose can be dissolved in a more simple manner, a method of manufacturing a cellulose precipitate in which cellulose can be recovered from the cellulose solution, and a method of saccharifying cellulose which uses the cellulose precipitate.

9 Claims, 1 Drawing Sheet

(56) References Cited

OTHER PUBLICATIONS

Alireza Monshizadeh, "Influence of the molecular weight of cellulose on the solubility in ionic liquid-water mixtures", A, Aalto University School of Science and Technology, Nov. 23, 2014, pp. 1-51.

Habahen Patel (M.Sc.), "Studies into the chemoenzymatic modification of cellulose by the laccase/TEMPO system", BOKU, Oct. 2010, pp. 1-116.

Gerald Perry E. Marin, "Carboxylated Cellulose Nanocrystals Extraction from Kraft Pulp Using Ammonium Persulfate as Low Cost Source & Sustainable Method for High Quality Flexible Packaging Bio-coating", Master's Thesis, 2015, pp. 1-63.

\* cited by examiner

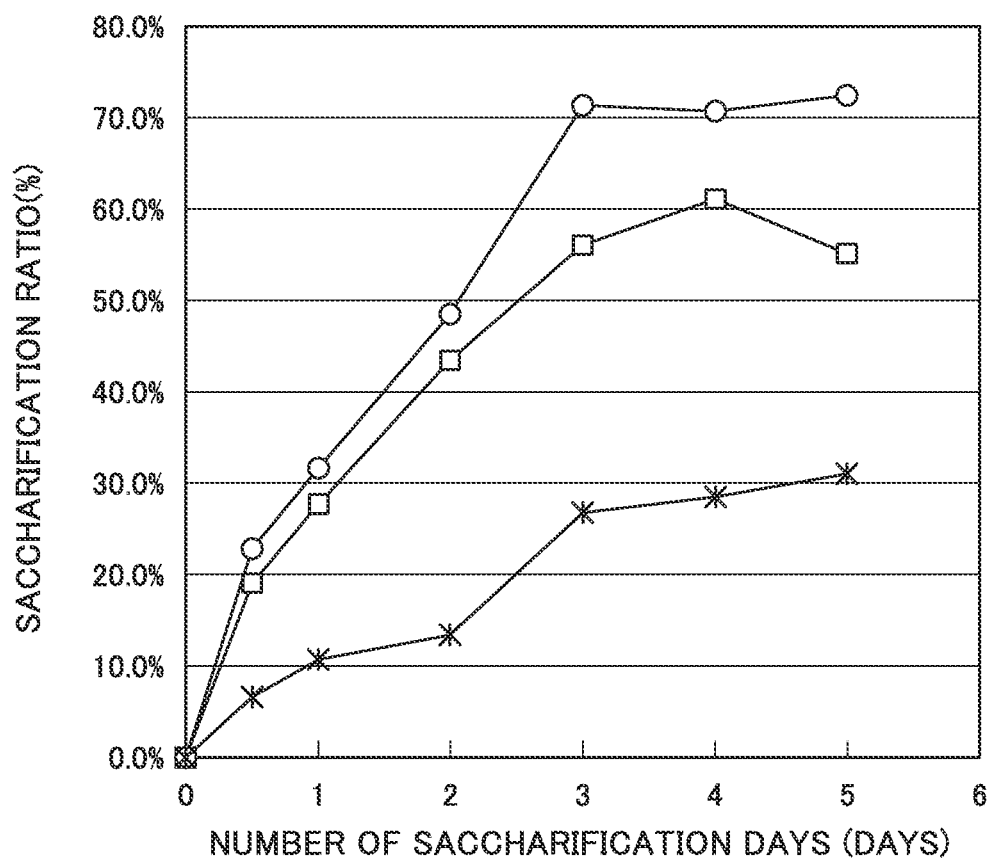

CELLULOSE SOLUTION MANUFACTURING METHOD, CELLULOSE PRECIPITATE MANUFACTURING METHOD, CELLULOSE SACCHARIFICATION METHOD, CELLULOSE SOLUTION, AND CELLULOSE PRECIPITATE

TECHNICAL FIELD

The present invention relates to a cellulose solution manufacturing method, a cellulose precipitate manufacturing method, a cellulose saccharification method, a cellulose solution, and a cellulose precipitate, and specifically to, a cellulose solution manufacturing method in which a cellulose-containing material such as cellulose-containing fiber products or product waste thereof is subjected to an ozonation treatment and an alkali treatment, a cellulose precipitate manufacturing method, a cellulose saccharification method, a cellulose solution, and a cellulose precipitate.

Priority is claimed on Japanese Patent Application No. 2010-214124, filed Sep. 24, 2010, the content of which is incorporated herein by reference.

BACKGROUND ART

Cellulose is a polysaccharide having 50 to 1000 or more glucose molecules linked together by β-glycosidic bond, and is also a main component of so-called wood-based biomass such as wood pulp or cotton. Studies for practical use of saccharides obtained by hydrolyzing cellulose, particularly, water-soluble oligosaccharides such as glucose as a raw material in manufacturing bioethanol through alcohol fermentation have been conducted in recent years (see PTL 1).

Generally, cellulose is insoluble in water and also hardly dissolves in an alkali aqueous solution. However, several solvents which can dissolve cellulose are known. For example, when cellulose is treated with a sodium hydroxide aqueous solution, a sodium salt of the cellulose is formed. When this salt is mixed with carbon disulfide, the mixture becomes sodium cellulose xanthate and becomes a colloidal dispersion solution which is referred to as viscose. Spun viscose rayon is formed by extruding the viscose into sulfuric acid. The cellulose constituting the viscose rayon has the same chemical composition as natural cellulose.

In addition, cellulose is also soluble in a cuprammonium solution. By extruding it into an acidic aqueous solution, cuprammonium rayon can be spun (see PTL 2).

In conventional cellulose solution manufacturing methods, carbon disulfide or a cuprammonium solution is used, and thus it is necessary to process waste water and the like, which causes a problem in that the environmental burden increases. In addition, when it is necessary to prevent the chemical substances from remaining in reproduced cellulose (rayon) to be obtained, it is also necessary to perform a rinsing treatment using a large amount of water.

CITATION LIST

Patent Literatures

[PTL 1] Japanese Unexamined Patent Application, First Publication No. 2001-95594
[PTL 2] Japanese Unexamined Patent Application, First Publication No. 2008-280635

SUMMARY OF INVENTION

Technical Problem

The present invention is contrived in view of the above-described circumstances and an object thereof is to provide a method of manufacturing a cellulose solution in which cellulose can be dissolved in a more simple manner, and the cellulose solution. In addition, another object of the invention is to provide a method of manufacturing a cellulose precipitate in which cellulose can be recovered from the cellulose solution, and the cellulose precipitate. A further object of the invention is to provide a method of saccharifying cellulose which uses the cellulose precipitate.

Solution to Problem

A cellulose solution manufacturing method according to a first aspect of the invention includes: performing an ozonation treatment to bring a cellulose-containing material and ozone into contact with each other; and performing an alkali treatment to bring the obtained treated material and an alkali aqueous solution into contact with each other, thereby dissolving at least cellulose in the cellulose-containing material in the alkali aqueous solution.

The cellulose solution manufacturing method according to a second aspect of the invention further includes: performing a drying treatment after the ozonation treatment to obtain the treated material in the first aspect.

In the cellulose solution manufacturing method according to a third aspect of the invention, a temperature of the drying treatment is 50° C. to 160° C. in the first or second aspect.

In the cellulose solution manufacturing method according to a fourth aspect of the invention, a concentration of the ozone is 1 mg/L to 300 mg/L, and a time of the ozonation treatment is 1 minute to 300 minutes in any one of the first to third aspects.

In the cellulose solution manufacturing method according to a fifth aspect of the invention, the alkali treatment includes bringing the treated material into contact with the alkali aqueous solution of 0.1 N to 10 N for a time range of 0.1 minutes to 60 minutes at a temperature range of −10° C. to 50° C. in any one of the first to fourth aspects.

A cellulose solution according to a sixth aspect of the invention is obtained using the manufacturing method according to any one of the first to fifth aspects.

A cellulose precipitate manufacturing method according to a seventh aspect of the invention includes: adjusting a pH of the cellulose solution obtained using the manufacturing method according to any one of the first to fifth aspects to pH 7 or less to precipitate and obtain cellulose.

A cellulose precipitate according to an eighth aspect of the invention is obtained using the manufacturing method according to the seventh aspect.

A cellulose saccharification method according to a ninth aspect of the invention includes: performing an enzymatic treatment to bring the cellulose precipitate obtained using the manufacturing method according to the seventh aspect and an aqueous solution containing a cellulolytic enzyme into contact with each other to thereby obtain an aqueous solution containing water-soluble oligosaccharides or glucose.

That is, the invention relates to the following.

(1) A cellulose solution manufacturing method including: performing an ozonation treatment to bring a cellulose-containing material and ozone into contact with each other; and performing an alkali treatment to bring the obtained treated material and an alkali aqueous solution into contact with each other, thereby dissolving at least cellulose in the cellulose-containing material brought into contact with the ozone in the alkali aqueous solution.

(2) The cellulose solution manufacturing method according to (1), further including: performing a drying treatment on the cellulose-containing material brought into contact with the ozone before the alkali treatment to obtain the treated material.

(3) The cellulose solution manufacturing method according to (1) or (2), in which a temperature of the drying treatment is 50° C. to 160° C.

(4) The cellulose solution manufacturing method according to any one of (1) to (3), in which a concentration of the ozone is 1 mg/L to 300 mg/L, and a time of the ozonation treatment is 1 minute to 300 minutes.

(5) The cellulose solution manufacturing method according to any one of (1) to (4), in which the alkali treatment includes bringing the treated material into contact with the alkali aqueous solution of 0.1 N to 10 N for a time range of 0.1 minutes to 60 minutes at a temperature range of −10° C. to 50° C.

(6) The cellulose solution manufacturing method according to any one of (1) to (5), in which the alkali aqueous solution is a sodium hydroxide aqueous solution.

(7) A cellulose solution which is obtained using the manufacturing method according to any one of (1) to (6).

(8) A cellulose precipitate manufacturing method including: adjusting a pH of the cellulose solution obtained using the manufacturing method according to any one of (1) to (7) to pH 7 or less to precipitate and obtain cellulose.

(9) A cellulose precipitate manufacturing method including: extruding the cellulose solution obtained using the manufacturing method according to any one of (1) to (7) into an acid aqueous solution.

(10) The cellulose precipitate manufacturing method according to (9), in which in the acid aqueous solution, a pH is 1.0 to 6.9 and a concentration is 1 wt % to 50 wt %.

(11) A cellulose precipitate which is obtained using the manufacturing method according to any one of (8) to (10).

(12) A cellulose saccharification method including: performing an enzymatic treatment to bring the cellulose precipitate obtained using the manufacturing method according to any one of (8) to (10) and an aqueous solution containing a cellulolytic enzyme into contact with each other to thereby obtain an aqueous solution containing water-soluble oligosaccharides or glucose.

Advantageous Effects of Invention

According to the cellulose solution manufacturing method of the invention, the cellulose-containing material as a raw material is subjected to the ozonation treatment and the alkali treatment to modify a crystallized part (cellulose crystals) of cellulose in the raw material, and thus a hydrophilic property can be improved. As a result, the cellulose in the raw material can be dissolved in the alkali aqueous solution.

The cellulose solution of the invention has a different chemical composition from known viscose. The viscose is a solution of cellulose derivatives including sulfur atoms derived from carbon disulfide which are required in the manufacturing process. On the other hand, the cellulose solution of the invention includes no sulfur atoms. Therefore, it can be used industrially as a cellulose solution with relatively small burden on the environment.

According to the cellulose precipitate manufacturing method of the invention, a cellulose precipitate formed of high-purity cellulose can be obtained. Even when the cellulose solution as a raw material includes impurities, cellulose can be preferentially precipitated by adjusting the pH of the cellulose solution to pH 7 or less.

In the case of the cellulose precipitate of the invention, since the cellulose has been dissolved once, micro-level fiber of the cellulose loosens with relative ease. Therefore, it is preferable as a raw material of the cellulose saccharification method, which can improve a conversion ratio of cellulose to glucose.

In addition, by extruding the cellulose solution of the invention into a solution of pH 7 or less, a cellulose precipitate spun into a thread-like form, or a film-like or spherical cellulose precipitate can also be obtained.

According to the cellulose saccharification method of the invention, a high-temperature, high-pressure pre-treatment is not needed and the cellulose precipitate is used as a raw material, and thus the hydrolysis rate of cellulose by the subsequent enzymatic treatment can be improved. In addition, in the enzymatic treatment, the cellulose is hydrolyzed under mild conditions, and thus water-soluble oligosaccharides or glucose of high purity, which are target products, can be obtained without generating overdegradation products of saccharides. The obtained water-soluble oligosaccharides or glucose of high purity are useful as a raw material of ethanol fermentation, lactate fermentation, or the like.

BRIEF DESCRIPTION OF DRAWINGS

FIG. 1 is a graph showing temporal changes of glucose conversion ratios in an enzymatic treatment.

DESCRIPTION OF EMBODIMENTS

Hereinafter, the invention will be described in detail.

<Cellulose Solution Manufacturing Method>

A cellulose solution manufacturing method of the invention is a method in which an ozonation treatment is performed to bring a cellulose-containing material and ozone into contact with each other and an alkali treatment is performed to bring the obtained treated material and an alkali aqueous solution into contact with each other, thereby dissolving at least cellulose in the cellulose-containing material in the alkali aqueous solution.

The cellulose solution manufacturing method of the invention may further include auxiliary treatments other than the above-described treatments.

<<Ozonation Treatment>>

In the invention, the cellulose-containing material is preferably cellulose-containing fiber, and more preferably fiber containing cotton because the effect of the invention is sufficiently obtained.

The cellulose-containing fiber is not particularly limited as long as it is a fibrous material containing cellulose. Examples of preferable cellulose-containing fibers include fibers which are used for clothing such as cotton, linen (ramie, flax, manila hemp, sisal hemp, kenaf, and the like), TENCEL (lyocell), rayon, and cupra, paper products such as copy paper, package paper, and cardboard, and the like. Cellulosic fibers blended with synthetic fibers such as polyesters and natural fibers such as silk may also be included.

Among them, cotton is preferable because it contains no impurities.

The form of the cellulose-containing fiber is not particularly limited, and cellulose-containing fibers processed into a cotton-like, thread-like, rope-like, cloth-like, planar, or three-dimensional form can be used.

Among them, a rope-like or cloth-like form is preferable from the viewpoint of ease in handling.

In addition, the cellulose content in the cellulose-containing material is preferably high from the viewpoint of increasing the purity of a cellulose solution to be manufactured.

The cellulose content is preferably 0.1 wt % to 30 wt %, more preferably 0.1 wt % to 20 wt %, and even more preferably 0.1 wt % to 10 wt %.

In the invention, the ozone is not particularly limited as long as it is in a state in which it is brought into contact with a cellulose-containing material. For example, gaseous ozone (ozone gas) or an ozone solution is preferable, and an ozone solution which is easy to handle is more preferable.

The ozone gas can be generated by irradiating the air with ultraviolet rays or performing silent discharge in the oxygen. When ozone gas is used in the invention, the ozone gas may be supplied from a known ozone generator. The ozone gas can be used as a mixed gas of air with ozone.

A solvent for the ozone solution is not particularly limited as long as it is a solvent which can dissolve ozone. However, water is preferable from the viewpoint of a reduction in the burden on the environment and ease of the waste water treatment.

That is, ozone water is preferable as the ozone solution of the invention. The ozone water can be supplied from a known ozone water generation device using electrolysis of water or the like.

In the ozonation treatment, the method of bringing the cellulose-containing material and the ozone into contact with each other is not particularly limited. Examples thereof include a method of causing contact by infusing ozone gas or an ozone solution to a pulverized cellulose-containing material, a method of causing contact by immersing the cellulose-containing material in the ozone solution, a method of causing contact by passing the ozone solution over a position at which the cellulose-containing material is located, and the like. Among them, a method of causing contact by immersing the cellulose-containing material in the ozone solution is preferable from the viewpoint of simplification of the structure of facilities.

As a specific example, there is a method including: putting the cellulose-containing material in an ozone-resistant basket; and immersing and shaking the basket in the ozone solution to perform the ozonation treatment.

The concentration of the ozone in the ozone gas or ozone solution which is brought into contact with the cellulose-containing material is preferably 1 mg/L to 300 mg/L, more preferably 20 mg/L to 250 mg/L, and even more preferably 40 mg/L to 200 mg/L.

When the concentration is equal to or greater than the lower limit value of the above-described range, the hydrogen bond of the cellulose in the cellulose in the cellulose-containing material can be weakened. When the concentration is equal to or lower than the upper limit value of the above-described range, the β-(1,4)-glycosidic bond (main chain) of the cellulose in the cellulose-containing material can be suppressed from being degraded.

In the ozonation treatment, the temperature at which the cellulose-containing material and the ozone are brought into contact with each other is preferably −10° C. to 50° C., more preferably −5° C. to 40° C., and even more preferably 0° C. to 30° C.

When the temperature is equal to or higher than the lower limit value of the above-described range and equal to or lower than the upper limit value of the above-described range, cellulose crystals in the cellulose in the cellulose-containing material are sufficiently modified and the subsequent alkali treatment can be more effectively performed.

In the ozonation treatment, regarding the treatment time during which the cellulose-containing material and the ozone are brought into contact with each other, the treatment can be generally performed within 48 hours. The treatment time of the zone treatment is preferably in the range of 0.1 minutes to 300 minutes, more preferably 1 minute to 200 minutes, and even more preferably 5 minutes to 100 minutes.

When the treatment time is equal to or greater than the lower limit value of the above-described range and within the upper limit value of the above-described range, cellulose crystals in the cellulose in the cellulose-containing material are sufficiently modified and the subsequent alkali treatment can be more effectively performed.

Regarding the properties of the cellulose-containing material included in the treated material obtained through the ozonation treatment, it may exhibit a slight white color, but there is almost no change after the ozonation treatment.

The cellulose in the cellulose-containing material generally has a crystallized part and a noncrystallized part. It is generally thought that the crystallized part is composed of microfibrils in which cellulose molecular chains are bound in parallel by hydrogen bond.

In the ozonation treatment, it is thought that the hydrogen bond is weakened by oxidation of a hydroxyl group using the oxidation power of the ozone. As a result, in the subsequent alkali treatment, the cellulose molecular chain and alkali are sufficiently brought into contact with each other, and thus the efficiency of the dissolution by the alkali treatment can be improved.

In the cellulose solution manufacturing method of the invention, the treated material obtained by further drying the cellulose-containing material obtained in the ozonation treatment is preferably used in the alkali treatment to be described later.

The drying is preferably performed until there is no variation in weight of the cellulose-containing material following evaporation of moisture.

The solubility of the treated material in the alkali treatment can be significantly increased by performing the drying treatment. It is presumed that the reason for this is that since the drying treatment promotes degradation of cellulose crystals in the cellulose-containing material, dissolution in the subsequent alkali treatment can be promoted.

The method of performing the drying treatment is not particularly limited as long as it is a method to dry the cellulose-containing material subjected to the ozonation treatment. Preferable examples thereof include a method of infusing warm air to perform drying and a method of perform drying using a heated-air dryer. Among the drying methods, a heated-air drying method is preferable.

The temperature of the drying treatment is preferably in the range of 50° C. to 160° C., and more preferably 100° C. to 140° C. When the temperature of the drying treatment is in the above-described range, the cellulose-containing material subjected to the ozonation treatment can be dried for a short time and thus there is less concern that the cellulose-containing material may be scorched.

When the temperature is lower than the lower limit value of the above-described range, the cellulose-containing material is not easily dried and takes a long time to dry, whereby there is concern that the drying treatment may become a bottleneck of the manufacturing process.

When the temperature is higher than the upper limit value of the above-described range, there is concern that the cellulose-containing material may be scorched.

The drying treatment time is determined in accordance with the amount of the cellulose-containing material which is dried at a time. The drying treatment is preferably performed until there is no variation in weight of the cellulose-containing material following evaporation of moisture.

The pressure in the drying treatment is preferably an ordinary pressure from the viewpoint of simplification of the processing device.

<<Alkali Treatment>>

The alkali aqueous solution in the alkali treatment of the invention is not particularly limited as long as it is an alkali aqueous solution which can dissolve at least the cellulose (cellulose molecular chains) in the treated material (the cellulose-containing material subjected to the ozonation treatment or the cellulose-containing material subjected to the ozonation treatment and the drying treatment). Examples thereof include an aqueous solution containing sodium hydroxide, ammonia water, an aqueous solution containing calcium hydroxide, and the like.

Among them, an aqueous solution containing sodium hydroxide is preferable. By using sodium hydroxide, cellulose can be converted into cellulose sodium salt adsorbed by sodium ions. As a result, the aggregation and hydrogen bond of the cellulose are suppressed, and thus the solubility of the cellulose in the alkali aqueous solution can be improved.

In the alkali treatment, the method of bringing the treated material and the alkali aqueous solution into contact with each other is not particularly limited. For example, a method of causing contact by immersing the treated material in the alkali aqueous solution may be employed. As a specific example, there is a method including: putting the treated material in an alkali-resistant basket; and immersing and shaking the basket in the alkali aqueous solution to perform the alkali treatment.

In the alkali treatment, when the alkali aqueous solution is a sodium hydroxide aqueous solution, the concentration thereof (normality) is preferably 0.1 N to 10 N, and more preferably 1 N to 5 N.

When the concentration is equal to greater than the lower limit value of the above-described range and equal to or less than the upper limit value of the above-described range, the treated material can be sufficiently dissolved.

In the alkali treatment, the temperature at which the treated material and the alkali aqueous solution are brought into contact with each other is preferably −10° C. to 50° C., and more preferably −5° C. to 30° C.

When the temperature is equal to or higher than the lower limit value of the above-described range and equal to or lower than the upper limit value of the above-described range, the treated material can be sufficiently dissolved.

In the alkali treatment, regarding the range of the treatment time during which the treated material and the alkali aqueous solution are brought into contact with each other, the treatment can generally be performed within 48 hours, preferably for 0.1 minutes to 60 minutes, and more preferably 1 minute to 30 minutes.

When the treatment time is equal to or greater than the lower limit value of the above-described range and within the upper limit value of the above-described range, the treated material can be sufficiently dissolved.

A cellulose solution in which at least the cellulose in the treated material is dissolved is obtained by the alkali treatment.

When substances which are originally insoluble in the alkali aqueous solution are included in the cellulose-containing material, there are cases in which these substances are not dissolved by the alkali treatment. These insoluble components are preferably removed using a known method such as filtration or centrifugal separation.

<<Cellulose Solution>>

A cellulose solution of the invention is a solution in which cellulose or cellulose salt is dissolved in the alkali aqueous solution.

Examples of the cellulose salt include monovalent cation salts such as sodium salts, potassium salts, or lithium salts of cellulose and divalent cation salts such as magnesium salts or calcium salts of cellulose. Among them, sodium salts or potassium salts are preferable from the viewpoint of the price of the chemicals.

Generally, the cellulose salt is formed by cations in the alkali aqueous solution used in the alkali treatment being adsorbed to the cellulose. In addition, the cellulose salt may be formed by salts derived from the cellulose-containing material.

The properties of the cellulose solution of the invention are as follows.

The polymerization degree of the cellulose molecular chain is 50 to 50,000.

When an alkali solution (4N-sodium hydroxide aqueous solution) is used as a solvent, the dissolution degree of the treated material including the cellulose is 1.0 mass % to 100 mass %.

When the dissolution degree is in the above range, the viscosity of the cellulose solution is 0.001 Pa·s to 1000 Pa·s.

The concentration of the cellulose in the cellulose solution is 0.1 mass % to 30 mass %, preferably 0.1 mass % to 20 mass %, and more preferably 0.1 mass % to 10 mass %.

In the cellulose solution of the invention, cellulose is dissolved in an alkali aqueous solution, and thus a transparent light yellow color is exhibited. When cellulose which is not subjected to the ozonation treatment is dispersed in the alkali aqueous solution, the solution yields a white turbidity. The white turbidity indicates that crystal components of the cellulose are not dissolved but dispersed in the alkali aqueous solution. The cellulose suspension yielding a white turbidity is clearly differentiated from the cellulose solution of the invention.

<<Cellulose Precipitate Manufacturing Method>>

A cellulose precipitate manufacturing method of the invention is a method to precipitate cellulose by adjusting the pH of the cellulose solution of the invention to pH 7 or less.

When cellulose is precipitated using a cellulose precipitate manufacturing method of the invention, the pH of the cellulose solution is preferably in the range of 1.0 to 6.9, more preferably 1.0 to 5.0, and even more preferably 1.0 to 3.0.

Various methods can be applied as a method to precipitate cellulose by adjusting the pH of the cellulose solution to pH 7 or less.

Examples thereof include the following methods.

Acid such as hydrochloric acid is added to the cellulose solution.

The cellulose solution is dripped or extruded into an acid solution such as hydrochloric acid.

The cellulose solution is dialyzed with respect to an acid solution such as hydrochloric acid.

Among them, a method of extruding the cellulose solution into an acid solution such as hydrochloric acid is preferable from the viewpoint that existing rayon manufacturing facilities can be utilized.

Specifically, for example, a cellulose precipitate can be obtained by extruding the cellulose solution into an acid solution.

The pH of the acid solution is preferably in the range of 1.0 to 6.9, more preferably 1.0 to 5.0, and even more preferably 1.0 to 3.0. The concentration of the acid solution is preferably in the range of 1 wt % to 50 wt %, more preferably 1 wt % to 30 wt %, and even more preferably 1 wt % to 20 wt %.

Examples of the acid solution include acid aqueous solutions, and specific examples thereof include 4N-hydrochloric acid.

The concentration of the cellulose solution is not particularly limited, and may be adjusted to, for example, 1 mass % to 80 mass %.

As the extrusion method, a method of ejecting the cellulose aqueous solution into the acid aqueous solution from pores (having a diameter of, for example, 1 mm to 10 mm) is used, and thus cellulose precipitates spun into a thread-like form can be obtained. In addition, cellulose precipitates formed into a film shape can be obtained by ejection from long pores (for example, 1 mm in length×300 mm in breadth) in the same manner. Furthermore, spherical (or massive, or ball-like) cellulose precipitates can be obtained by dripping the cellulose solution into the acid aqueous solution with one dripping amount set to, for example, 0.05 ml to 0.5 ml.

By appropriately adjusting the pressure at the time of extrusion or the concentration of the cellulose solution, these cellulose precipitates can also be obtained as cellulose precipitates in which cellulose fiber loosens relatively easily, or which have high water absorbability.

Even when impurities other than cellulose are mixed in the cellulose solution, the cellulose in the cellulose solution can be preferentially precipitated in the acid aqueous solution while the impurities are dissolved, as long as the impurities are substances which are soluble in the acid aqueous solution. That is, the cellulose purity of the cellulose precipitate can be increased in the course of precipitation.

For example, when cellulose in the cellulose solution forms salt with cations, the cellulose and cations which form the salt are dissociated from each other in the acid aqueous solution. In other words, cellulose is precipitated by treating the cellulose salt with the acid aqueous solution.

The obtained cellulose precipitate is preferably washed with pure water to remove acid components and impurities.

<<Cellulose Precipitate>>

A cellulose precipitate of the invention is a precipitate which is obtained using the above-described cellulose precipitate manufacturing method according to the invention.

The cellulose constituting the cellulose precipitate is dissolved once in a cellulose solution. Therefore, it has high dispersibility in an aqueous solution and is thus preferable as a raw material in a cellulose saccharification method to be described later.

<<Cellulose Saccharification Method>>

A cellulose saccharification method of the invention is a method of obtaining an aqueous solution containing water-soluble oligosaccharides or glucose by performing an enzymatic treatment in which the cellulose precipitate of the invention and an aqueous solution containing a cellulolytic enzyme are brought into contact with each other.

The cellulolytic enzyme generates glucose by hydrolyzing β-(1,4)-glycosidic bond of cellulose molecules. In order to develop the hydrolysis reaction, it is necessary to adsorb the enzyme to a predetermined position in the cellulose molecular chain.

When normal cellulose is used as a substrate, some cellulose molecular chains in the substrate constitute cellulose crystals (crystallized part), and thus in this crystallized part, adsorption of the cellulose enzyme to the predetermined position is disrupted. As a result, in the cellulose as a raw material, the efficiency of hydrolyzing the crystallized part is reduced.

The cellulose precipitate preferably contains impurities which are likely to inhibit the saccharification reaction as little as possible, from the viewpoint of increasing a conversion ratio of the cellulose to the saccharides. That is, the cellulose content in the cellulose precipitate is preferably high.

The cellulose content in the cellulose precipitate is preferably 50 wt % to 100 wt %, more preferably 60 wt % to 100 wt %, and even more preferably 80 wt % to 100 wt %.

The pH of the cellulose precipitate is preferably adjusted to close to the optimum pH of the cellulolytic enzyme being used. For example, the cellulose precipitate is preferably washed with water or an acid aqueous solution. As a method of washing the cellulose precipitate, for example, a method of immersing and washing the cellulose precipitate in deionized water and/or an acid aqueous solution may be employed. Otherwise, it may be washed by passing deionized water and/or an acid aqueous solution over a position at which the cellulose precipitate is located. As a specific example, there is a method including: putting the cellulose precipitate in a basket; immersing and shaking the basket in deionized water and/or an acid aqueous solution; and appropriately exchanging the deionized water and/or the acid aqueous solution.

The acid aqueous solution is not particularly limited as long as it is a solution which does not inhibit the subsequent enzyme reaction. Preferable examples thereof include an acetate buffer solution, a citrate buffer solution, a phosphate buffer solution, and the like, and an acetate buffer solution is particularly preferable.

The pH range of the acid aqueous solution is close to the optimum pH of the cellulolytic enzyme being used and may be a range in which the subsequent enzyme reaction is not inhibited. The pH is preferably in the range of pH 2.0 to pH 6.9, more preferably pH 3.0 to pH 6.9, and even more preferably pH 4.0 to pH 6.0.

The pH of the acid aqueous solution is preferably in this range, because the pH of the aqueous solution contained in the washed cellulose precipitate can be matched with the optimum pH (generally, pH 4 to 6) of the subsequent enzyme reaction.

The concentration of the acid aqueous solution may be appropriately adjusted.

The method of bringing the cellulose precipitate washed with the water and/or the acid aqueous solution and the aqueous solution containing the cellulolytic enzyme into contact with each other is not particularly limited. For example, a method of causing contact by immersing the cellulose precipitate in the aqueous solution containing the cellulolytic enzyme may be employed. Otherwise, these may be brought into contact with each other by passing the aqueous solution containing the cellulolytic enzyme. As a specific example, there is a method including: putting the cellulose precipitate in a basket; and immersing and shaking the basket in the aqueous solution containing the cellulolytic enzyme to perform the enzymatic treatment.

The cellulolytic enzyme is not particularly limited as long as it is an enzyme which can hydrolyze the cellulose to generate water-soluble oligosaccharides or glucose, and known cellulolytic enzymes (cellulase) may be used in a predetermined amount. Here, the water-soluble oligosaccharides indicate water-soluble cello-oligosaccharides having a molecular structure in which glucose of about 2 to 6 molecules is condensed and connected.

Examples of known cellulolytic enzymes include Cellulase SS (manufactured by Nagase ChemteX Corporation), Meicelase (manufactured by Meiji Seika Kaisha, Limited), Enzylon (manufactured by Rakuto Kasei Industrial Co., Ltd.), and the like. Among them, Cellulase SS is preferable.

For example, the enzyme activity of Cellulase SS is 1600 CUN/g.

The aqueous solution containing the cellulolytic enzyme preferably contains a pH buffer for pH stabilization. It is desirable that the pH of the aqueous solution is close to the optimum pH (pH at which the enzyme activity increases) of the cellulolytic enzyme. Generally, since the optimum pH is acidic to neutral in many cases, an acetate buffer solution, a citrate buffer solution, a phosphate buffer solution, or the like is preferably used, and an acetate buffer solution is particularly preferable.

In the enzymatic treatment, it is desirable that the temperature at which the cellulose precipitate and the aqueous solution containing the cellulolytic enzyme are brought into contact with each other is close to the optimum temperature (temperature at which the enzyme activity increases) of the cellulolytic enzyme. The optimum temperature is generally in the range of 10° C. to 80° C., preferably 40° C. to 70° C., and more preferably 50° C. to 65° C.

In the enzymatic treatment, the pH at which the cellulose precipitate and the aqueous solution containing the cellulolytic enzyme are brought into contact with each other is preferably 3 to 8, more preferably 4 to 7, and even more preferably 5 to 6.

In the enzymatic treatment, regarding the range of the treatment time during which the cellulose precipitate and the aqueous solution containing the cellulolytic enzyme are brought into contact with each other, the treatment can be performed within 14 days at the appropriate enzyme concentration, pH, and temperature. In many cases, the reaction rate is the highest during 1 day after starting the reaction, and then the reaction rate gradually decreases during 2 to 6 days. After 10 days from the start of the reaction, the reaction almost stops and a conversion ratio of the cellulose contained in the cellulose precipitate to glucose tends to hit a peak.

Here, the conversion ratio indicates a ratio of the mass of the saccharides obtained by the saccharification reaction to the mass of the cellulose contained in the cellulose precipitate. The saccharides indicate the water-soluble oligosaccharides or glucose.

In the cellulose saccharification method of the invention, since the cellulose is hydrolyzed using an enzyme under relatively mild conditions, high-purity saccharides can be obtained. The generated saccharides are dissolved in the aqueous solution containing the cellulolytic enzyme. The method of recovering and obtaining the saccharides from the aqueous solution is not particularly limited, and the recovery may be performed using a known method such as chromatography.

EXAMPLES

Next, the invention will be described in more detail using examples. However, the invention is not limited to the examples.

Example 1

100 g of cotton thread as a cellulose-containing material was brought into contact with ozonated water of 50 mg/L three times for 60 minutes, and then a drying treatment was performed for 1 hour at 130° C., thereby removing the ozone.

5 g of the obtained treated material and 200 g of a 4N-sodium hydroxide aqueous solution were mixed in a beaker (300 mL) made of glass and brought into contact with each other for 30 minutes at 25° C.

As a result of the test, it was visually confirmed that the treated material was completely dissolved. The obtained cellulose solution exhibited a transparent light yellow color.

Example 2

Ozone gas (gas mixed with the air) of 200 mg/L was infused and brought into contact with 100 g of cotton thread as a cellulose-containing material for 10 minutes, and then a drying treatment was performed for 1 hour at 130° C., thereby removing the ozone.

5 g of the obtained treated material and 200 g of a 4N-sodium hydroxide aqueous solution were mixed in a beaker (300 mL) made of glass and brought into contact with each other for 60 minutes at 25° C.

As a result of the test, it was visually confirmed that the treated material was completely dissolved. The obtained cellulose solution exhibited a transparent light yellow color.

Example 3

The cellulose solution obtained in Example 2 was extruded from the tip of a syringe needle into a hydrochloric acid bath of pH 1.0 and a thread-like cellulose precipitate of about $\phi$0.1 mm×about 1 m in length was obtained.

Comparative Example 1

The process was performed in the same manner as in Example 1, except for substituting the ozonated water with ion-exchange water. In other words, the ozonation treatment was not performed and only the alkali treatment was performed.

As a result of the test, it was visually confirmed that the cellulose was not dissolved. The sodium hydroxide aqueous solution after the alkali treatment was a cloudy solution.

Example 4

The cellulose precipitate obtained in Example 3 was left for 8 hours by being immersed in deionized water. An amount equivalent to 0.5 g in terms of dry weight was separated from the water-washed cellulose precipitate and a sodium acetate buffer solution (pH 5.0) was added thereto, thereby obtaining a sample A (pH 5.0).

Next, 0.2 ml of Cellulase SS (manufactured by Nagase ChemteX Corporation; 1600 CUN/g or greater in activity) as a cellulolytic enzyme was added to the sample A to bring the cellulose precipitate and the enzyme into contact with each other. The sample A was placed without being shaken by a shaker, and held at 40° C.

After starting the enzymatic treatment, the amount of glucose contained in the reaction solution after the lapse of a predetermined number of days was measured through HPLC, and the following formula "glucose conversion ratio (mass %)=mass of generated glucose/mass of cellulose precipitate (0.5 g)" was calculated.

As a result of the test, the glucose conversion ratio was 32% after 1 day, 49% after 2 days, and 72% after 3 days. The result was plotted by "○" in FIG. 1.

The saccharification ratio shown in FIG. 1 is synonymous with the glucose conversion ratio described above.

Comparative Example 2

The process was performed in the same manner as in Example 4, except that a filtered material obtained by filtering the cloudy solution of Comparative Example 1 was sufficiently washed with deionized water.

As a result of the test, the glucose conversion ratio was 28% after 1 day, 44% after 2 days, and 58% after 3 days. The result was plotted by "∪" in FIG. 1.

Comparative Example 3

5 g of cotton thread as a cellulose-containing material was sufficiently washed with deionized water and an amount equivalent to 0.5 g in terms of dry weight was separated therefrom and used as a substrate to perform an enzymatic treatment in the same manner as in Example 4.

As a result of the test, the glucose conversion ratio was 11% after 1 day, 13% after 2 days, and 28% after 3 days. The result was plotted by "*" in FIG. 1.

From the above results, it was confirmed that Example 4 according to the invention had a significantly higher glucose conversion ratio than Comparative Examples 2 and 3. It is thought that such a result is due to the fact that since the surface area of the cellulose precipitate is greater than the cotton thread, water absorbability increases.

INDUSTRIAL APPLICABILITY

A cellulose solution manufacturing method, a cellulose precipitate manufacturing method, a cellulose saccharification method, a cellulose solution, and a cellulose precipitate of the invention can be widely used to manufacture saccharides from a cellulose-containing material.

The invention claimed is:

1. A cellulose solution manufacturing method comprising:
providing a cellulose-containing material, wherein said cellulose-containing material comprises at least one of cotton, lyocell, rayon, and cupra;
contacting said cellulose-containing material with ozone to obtain an ozonated cellulose-containing material;
drying said ozonated cellulose-containing material at a temperature in the range of 50° C. to 160° C. to obtain a dried treated material;
mixing said dried treated material with a 1N to 5N sodium hydroxide aqueous solution to obtain a mixture; and
maintaining said mixture at a temperature of −10° C. to 50° C. for 0.1 minute to 60 minutes to dissolve at least cellulose and obtain a cellulose solution comprising dissolved cellulose having a polymerization degree of 50 to 50,000.

2. The method of claim 1, wherein said ozone is present at a concentration of 1 mg/L to 300 mg/L, and a time of contacting said cellulose-containing material with said ozone is 1 minute to 300 minutes.

3. The method of claim 1, further comprising:
adjusting a pH of said cellulose solution to pH 7 or less to precipitate and obtain a cellulose precipitate.

4. The method of claim 1, further comprising:
extruding said cellulose solution into an acid aqueous solution to obtain a cellulose precipitate.

5. The method of 4, wherein said acid aqueous solution has a pH from 1.0 to 6.9 and a concentration of acid from 1 wt % to 50 wt %.

6. The method of claim 3, further comprising:
saccharifying said cellulose precipitate in the presence of a cellulolytic enzyme to thereby obtain an aqueous solution containing water-soluble oligosaccharides or glucose.

7. The method of claim 1, wherein said dissolved cellulose in said cellulose solution is capable of forming a cellulose precipitate having a cellulose content of 50 wt % to 100 wt %.

8. The method of claim 1, wherein said temperature of said mixture is maintained at −5° C. to 30° C. for 1 minute to 30 minutes.

9. A cellulose solution manufacturing method comprising:
providing a cellulose-containing material, wherein said cellulose-containing material comprises at least one of cotton, lyocell, rayon, and cupra;
contacting said cellulose-containing material with ozone to obtain an ozonated cellulose-containing material;
drying said ozonated cellulose-containing material at a temperature in the range of 50° C. to 160° C. to obtain a dried treated material;
mixing said dried treated material with an aqueous solution consisting of 1N to 5N sodium hydroxide and water to obtain a mixture; and
maintaining said mixture at a temperature of −10° C. to 50° C. for 0.1 minute to 60 minutes to dissolve at least cellulose and obtain a cellulose solution comprising dissolved cellulose having a polymerization degree of 50 to 50,000.

* * * * *